(12) United States Patent
Narula et al.

(10) Patent No.: US 7,485,668 B2
(45) Date of Patent: *Feb. 3, 2009

(54) CYCLOPROPANATED MACROCYCLIC KETONES AND LACTONES

(75) Inventors: Anubhav P. S. Narula, Hazlet, NJ (US); Edward Mark Arruda, Cliffwood, NJ (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 288 days.

This patent is subject to a terminal disclaimer.

(21) Appl. No.: 11/386,957

(22) Filed: Mar. 22, 2006

(65) Prior Publication Data

US 2006/0234885 A1 Oct. 19, 2006

Related U.S. Application Data

(63) Continuation-in-part of application No. 11/105,626, filed on Apr. 14, 2005, now Pat. No. 7,189,881.

(51) Int. Cl.
*A01N 35/00* (2006.01)
*A61K 31/12* (2006.01)
*C07D 49/00* (2006.01)

(52) U.S. Cl. ...................... 514/691; 568/374
(58) Field of Classification Search ................. 568/374; 514/691

See application file for complete search history.

(56) References Cited

U.S. PATENT DOCUMENTS

| | | | |
|---|---|---|---|
| 4,262,124 | A | 4/1981 | Scholes et al. |
| 4,278,817 | A | 7/1981 | Lamparsky et al. |
| 4,282,274 | A | 8/1981 | Mookherjee et al. |
| 4,720,354 | A | 1/1988 | Asakawa et al. |
| 7,189,881 | B2 * | 3/2007 | Narula et al. ............... 568/374 |

FOREIGN PATENT DOCUMENTS

| | | |
|---|---|---|
| DE | 101 52 990 A1 | 5/2003 |
| WO | WO 03/053902 A1 | 7/2000 |
| WO | WO 2004/083357 A1 | 9/2004 |

OTHER PUBLICATIONS

Cope et al. Journal of the American Chemical Society (1962), 84, pp. 4843-4849.*
Cope et al. Journal of the American Chemical Society (1962), 84, pp. 4850-4855.*
Gassman et al. Journal of the American Chemical Society (1989), 111(7), pp. 2652-2662.*
Auclair et al. Journal of the American Chemical Society (2002), pp. 124(21), 6020-6027.*
"Diastereoselective Manipulations of Bicyclo [m.1.0]alkane Derivatives. Nucleophilic Additions to the Carbonyl Carbons of Bicyclo [m.1.0]alkan-2-ones," Eugene A. Mash, Timothy M. Gregg, and Michelle A. Kaczynski; Journal of Organic Chemistry 1996, 61, 2743-2752.
"Development of Molecular Mechanics Torison Parameters for α,β-cyclopropyl ketones and conformational analysis of bicycle [m.1.0]alkan-2-ones," Eugene A. Mash, Timothy M. Gregg, Matthew T. Stahl, and W. Patrick Walters; Journal of Organic Chemistry 1996, 61, 2738-2742.
"Diastereoselective Manipulations of Bicyclo[m.1.0]alkane Derivatives. Reactions of Nucleophiles with Bicyclo[m.1.0]alk-3-en-2-ones," Eugene A. Mash, Timothy M. Gregg, and James A. Brown; Journal of Organic Chemistry 1997, 62, 8513-8521.
Wiberg, Kenneth B. et al: "Cis- and trans-Bicyclo[6.1.0]nonan-2(3 and 4)-ones", Tetrahedron Letters, (1), 59-62 Coden: Teleay; ISSN: 0040-4039, 1969, XP002389809, p. 59-60, compounds II, III, V, VI.
Moon, Sung et al: "Photochemistry of biyclclo[6.1.0]nonan-3-one, bicycle [6.1.0]nonan-4-one, and cyclooctanone", Journal of Organic Chemistry, 36(10), 1434-8 Coden: Joceah; ISSN: 0022-3263, 1971, XP002389805, p. 1434. 1436, compound (1).
Lambert, Joseph B. et al: "Solvolysis of cis-bicyclo [5.1.0]oct-4-en-3-yl tosylate" Journal Of Organic Chemistry, 37(3) , 374-7 Coden: Joceah; ISSN: 0022-3263, 1972, XP002389803, p. 375, 376, compound 5.
Lambert, Joseph B. et al: "Competitive solvolytic homoconjugation" Journal Of The American chemical Society, 95(95), 1570-7 Coden: Jacsat; ISSN; 0002-7863,1973, XP002389800, p. 1572, 1576-7, compound 13.
Proksch, Ehrhardt et al: "Oxidation of cyclopropyl hydrocarbons with ozone" Angewandter Chemie, 88(23), 802-3 Coden: Ancead; ISSN: 0044-8249, 1976, XP002389806, p. 761, compounds (8) and (9).

(Continued)

*Primary Examiner*—D. Margaret Seaman
*Assistant Examiner*—Niloofar Rahmani
(74) *Attorney, Agent, or Firm*—Elizabeth M. Quirk; XuFan Tseng; Joseph F. Leightner

(57) ABSTRACT

The present invention is directed to novel cyclopropanated macrocyclic ketone and lactone compounds of the general formula

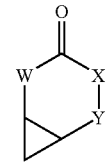

wherein X is an atom or a functional group selected from the group consisting of O, N, S, CH, or $CH_2$;
wherein Y is a straight or branched hydrocarbon moiety consisting of 1 to 20 carbon atoms;
wherein W is a straight or branched hydrocarbon moiety of consisting of 1 to 20 carbon atoms; and
wherein O is an oxygen atom;
and the use of these novel compounds in creating fragrances, and scents in items such as perfumes, colognes and personal care products.

6 Claims, No Drawings

OTHER PUBLICATIONS

Detty, Michael R. et al: "The fate of bishomocycloheptadienyl cations generated by deamination" Jornal Of The American Chemical Society, 99(3), 834-42 Coden: Jacsar; ISSN: 0002-7863, 1977, XP002389801, p. 836, compounds 29, 39, 44.

Karpf, Martin et al: "Sterospecific transformation of 2, 2-dimethylcyclobutanols into optically active 1,2-cis-disubstituted cyclopropanes", Journal Of The American Chemical Society, 103(2), 302-6 Coden: Jacsat; ISSN: 0002-7863, 1981, XP002389804, p. 303, 306, compound (18).

Hanold, Norbet et al: "Unsymmetrical cyclooctadienynes: 1,3-cyclooctadien-5-yne and 1,6-cyclooctadien-3-yne", Chemische Berichte, 188(1), 198-209, Coden: Chbeam: ISSN: 0009-2940, 1985, XP002389807, p. 201, compounds 36, 41.

Gassman, Paul G. et al: "Molecules with twist bent bonds. The synthesis, properties, and reactions of trans-bicyclo [4.1.0]hept-3-ene and certain methylated derivatives", Journal Of The American chemical Society, 111(7), 2652-62 Coden: Jacsat; ISSN: 0002-7863, 1989, XP002389802, p. 2654, 2660, compound 34.

Ward, Harry D. et al: "Ring expansions of 1,9,10 simple cyclic conjugated cyclopropyl ketones by the Nozaki method ate not regiospecific" Journal Of Organic Chemicstry, 57(6), 1926-8 Coden: Joceah; ISSN: 0022-3263, 1992, XP002389808, p. 1927, compound 22.

Auclair, Karine et al: "Revisiting the Mechanism of P450 Enzymes with the Radical Clocks Norcarane and Spiro [2,5] octane" Journal Of The American Chemical Society, 124 (21), 6020-6027 Coden; Jacsat; ISSN: 0002-7863, 2002, XP002389799, p. 6022, fig. 5, compound 17.

* cited by examiner

CYCLOPROPANATED MACROCYCLIC KETONES AND LACTONES

RELATED APPLICATION

This application is a continuation-in-part of the U.S. application Ser. No. 11/105,626, filed Apr. 14, 2005, now U.S. Pat. No. 7,189,881.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel cyclopropanated macrocyclic compounds, represented by the general structure of Formula I set forth below:

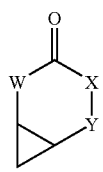

Formula I wherein X is an atom or a functional group selected from the group consisting of O, N, S, CH, or $CH_2$;

wherein Y is a hydrocarbon moiety consisting of 1 to 20 carbon atoms and containing single and/or double bonds;

wherein W is a hydrocarbon moiety of consisting of 1 to 20 carbon atoms and containing single and/or double bonds;

wherein O is an oxygen atom.

Another embodiment of the invention is a method for enhancing a perfume by incorporating an olfactory acceptable amount of the compounds provided above.

Another embodiment of the invention is a method for enhancing a perfume by incorporating an olfactory acceptable amount of the compound of structure below:

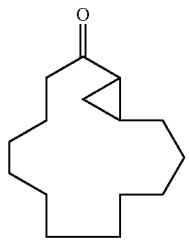

Formula II

These and other embodiments of the present invention will be apparent by reading the following specification.

DETAILED DESCRIPTION OF THE INVENTION

In Formula I above, Y and W represent straight or branched hydrocarbon moieties consisting of 1 to 20 carbon atoms and containing single and/or double bonds. Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like. Suitable hydrocarbon moieties containing double bonds include ethene, propene, 1-butene, 2-butene, penta-1-3-deine, hepta-1,3,5-triene and the like.

In the preferred embodiment of the invention, the novel compounds of the present invention are represented by the following structures:

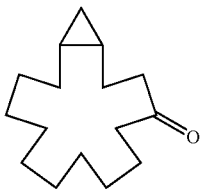

Formula III

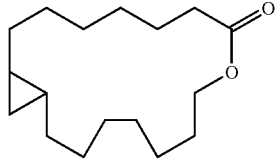

Formula IV

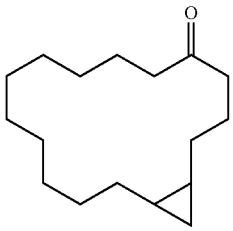

Formula V

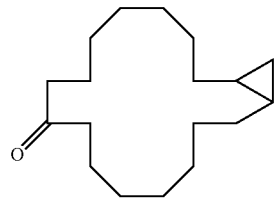

Formula VI

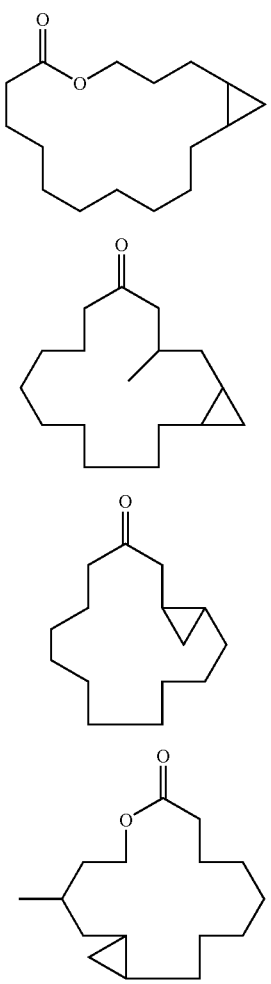

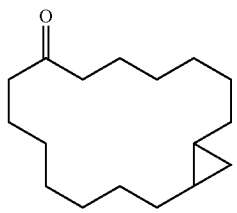

Those with the skill in the art will appreciate that the compound of Formula III is Bicyclo[13.1.0]hexadecan-4-one, the compound of Formula IV is 9-Oxa-bicyclo[15.1.0]octadecan-8-one, the compound of Formula V is Bicyclo[14.1.0]heptadecan-5-one, the compound of Formula VI is Bicyclo[15.1.0]octadecan-9-one and the compound of Formula VII is 5-Oxa-bicyclo[14.1.0]heptadecan-6-one, the compound of Formula VIII is 3-Methyl-bycyclo[13.1.0]hexadecane-5-one, the compound of Formula IX is Bicyclo[12.1.0]pentadecan-3-one, the compound of Formula X is 3-Methyl-6-oxa-bicyclo[13.1.0]hexadecane-7-one and the compound of Formula XI is Bicyclo[14.1.0]heptadecan-8-one.

The table below lists additional compounds derived from Formula I that are described in the present invention:

| W | Y | X | Compound |
|---|---|---|---|
| $CH_2$ | $(CH_2)_4$ | $CH_2$ | Bicyclo[7.1.0]decan-3-one |
| $CH_2$ | $(CH_2)_5$ | $CH_2$ | Bicyclo[8.1.0]undecan-3-one |
| $(CH_2)_3$ | $(CH_2)_5$ | $CH_2$ | Bicyclo[10.1.0]tridecan-5-one |
| $(CH_2)_5$ | $(CH_2)_5$ | $CH_2$ | Bicyclo[12.1.0]pentadecan-7-one |
| $(CH_2)_5$ | $(CH_2)_5$ | $CH_2$ | Bicyclo[13.1.0]hexadecan-7-one |
| $CH_2$ | $(CH_2)_5$ | O | 4-Oxa-bicyclo[8.1.0]decan-3-one |
| $CH_2$ | $(CH_2)_5$ | S | 4-Thia-bicyclo[8.1.0]decan-3-one |
| $(CH_2)_5$ | $(CH_2)_5$ | O | 7-Oxa-bicyclo[12.1.0]pentadecan-8-one |
| $(CH_2)_5$ | $(CH_2)_5$ | S | 7-Thia-bicyclo[12.1.0]pentadecan-8-one |
| $(CH_2)_5$ | $CH(CH_2)_4$ | CH | Bicyclo[12.1.0]pentadec-8-en-7-one |
| $(CH_2)_9$ | $C(CH_3)HCH_2$ | $CH_2$ | 3-Methyl-bicyclo[13.1.0]hexadecane-5-one |
| $(CH_2)_9$ | $C(CH_2CH_3)HCH_2$ | $CH_2$ | 3-Ethyl-bicyclo[13.1.0]hexadecane-5-one |
| $(CH_2)_9$ | $C(CH_3)HCH_2$ | O | 3-Methyl-4-oxa-bicyclo[13.1.0]hexadecane-5-one |
| $(CH_2)_9$ | $C(CH_2CH_3)HCH_2$ | O | 3-Ethyl-4-oxa-bicyclo[13.1.0]hexadecane-5-one |
| $(CH_2)_9$ | $C(CH_3)HCH_2$ | S | 3-Methyl-4-thia-bicyclo[13.1.0]hexadecane-5-one |
| $(CH_2)_9$ | $C(CH_2CH_3)HCH_2$ | S | 3-Ethyl-4-thia-bicyclo[13.1.0]hexadecane-5-one |
| $(CH_2)_9$ | $C(CH_3)HCH_2$ | N | 3-Methyl-4-aza-bicyclo[13.1.0]hexadecane-5-one |

-continued

| W | Y | X | Compound |
|---|---|---|----------|
| (CH$_2$)$_9$ | C(CH$_2$CH$_3$)HCH$_2$ | N | 3-Ethyl-4-aza-bicyclo[13.1.0]hexadecane-5-one |
| (CH$_2$)$_8$CH(CH$_3$) | (CH$_2$)$_3$ | O | 15-Methyl-5-oxa-bicyclo[14.1.0]heptadecan-6-one |
| (CH$_2$)$_8$CH(CH$_2$CH$_3$) | (CH$_2$)$_3$ | O | 15-Ethyl-5-oxa-bicyclo[14.1.0]heptadecan-6-one |
| (CH$_2$)$_6$(CH)$_2$CH(CH$_3$) | (CH$_2$)$_3$ | O | 15-Methyl-5-oxa-bicyclo[14.1.0]heptadec-13-en-6-one |

The compounds of the present invention may be prepared from the corresponding alkenes, via Simmons-Smith cyclopropanation reaction. As described in the Examples below, compounds of Formulae III-XI may be prepared via Simmons-Smith cyclopropanation reaction from the corresponding alkenes of the compounds below:

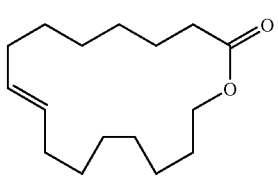

Formula XII

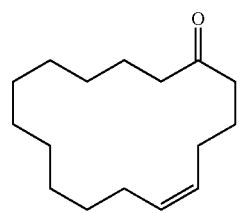

Formula XIII

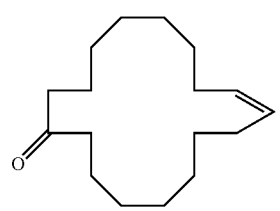

Formula XIV

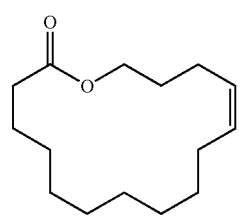

Formula XV

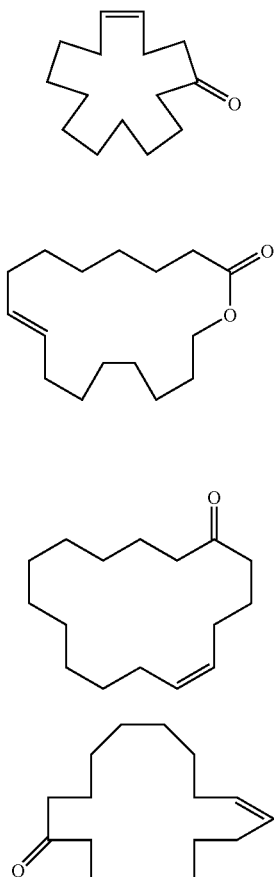

Formula XVI

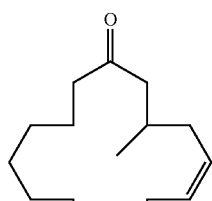

Formula XVII

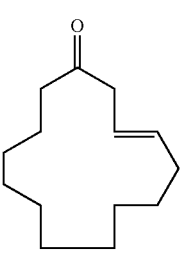

Formula XVIII

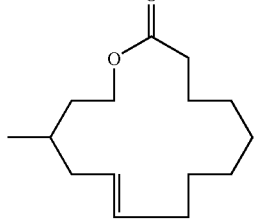

Formula XIX

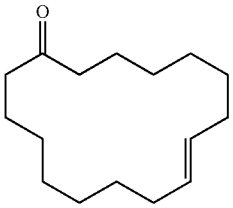

Formula XX

The alkenes of Formulae XII-XX are commercially available fragrance products. The compound of Formula XII is cyclopentadec-4-enone and is available from International Flavors & Fragrances Inc., New York, N.Y. under the trade name Musk Z-4. The compound of Formula XIII is oxacycloheptadec-9-en-2-one and is available from International Flavors & Fragrances Inc., New York, N.Y. under the trade name Ambrettolide. The compound of Formula XIV is cyclohexadec-5-enone and is commercially available under the trade names Velvione and Ambretone. The compound of Formula XV is cycloheptadec-9-enone is commercially available under the trade name Civettone. The compound of Formula XVI is oxacyclohexadec-12-en-2-one. The compound of Formula XVII is 3-methyl-5-cyclopentadecene-1-one and is commercially available under the trade name of Muscenone. Preparation of 3-methyl-5-cyclopentadecene-1-one is described in U.S. Pat. No. 6,720,303. The compound of formula XVIII is cyclotetradec-2- and or 3-ene-1-one and is available from the International Flavors & Fragrances Inc. The compound of Formula XIX is 12-methyl-14-cyclotetradec-9-enolide, preparation of which is described in EP 908 455 A1. The compound of Formula XX is a cyclohexadec-3-enone and is commercially available from Symrise under the trade name Globanone.

Those with skill in the art will recognize that the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

We have discovered that the compounds of Formulae III-X have a musk, sweet, powdery, floral tones that are well suited for use as a fragrance ingredient.

We have also discovered that a mixture of the compound of Formula XI and its precursor, the compound of Formula XX, a mixture of bicyclo[14.1.0]heptadecan-8-one and cyclohexadec-3-enone, possesses olfactory properties that are superior to those of the above pure compounds when taken alone. For example, the mixture of bicyclo[14.1.0]heptadecan-8-one and cyclohexadec-3-enone at a ratio of 7:3 exhibits stronger sweet floral tones than pure bicyclo[14.1.0]heptadecan-8-one or pure cyclohexadec-3-enone. The preferred ratio of the compound of the present invention to its precursor is from about 1.5:1 to about 4:1. The most preferred ratio is 3:1.

Another embodiment of the invention is a method for enhancing a perfume by incorporating an olfactory acceptable amount of the compound of structure below:

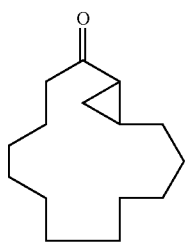

Formula II

Preparation of the compound of Formula II is described in Eugene A. Mash et al., Journal of Organic Chemistry 61, page 2743, year 1996.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc.

EXAMPLE A

Preparation of Bicyclo[13.1.0]hexadecan-4-one

To a dry 500 ml multi-neck round bottom flask fitted with an air stirrer, nitrogen inlet condenser and an addition funnel 2.7 g of 94% 4-cyclopentadecen-1-one and 50 ml of Methyl Tertiary Butyl Ether (MTBE) was added. The resulting mixture was stirred for 5 minutes. 21.8 ml of 1.1 M $Et_2Zn$ were added slowly. The temperature of the mixture rose to 35° C. After the temperature of the mixture stabilized, 23 g of $CH_2I_2$ were added while stirring. The mixture was heated to 60° C. In about 60 minutes a first sample of the product was taken. The mixture was left to age overnight. Next morning, the mixture was quenched with saturated $NH_4Cl$, aqueous layer separated and the organic layer washed with $NaHCO_3$. The organic layer was then dried over anhydrous $MgSO_4$.

The gas chromatography test indicated that 74.4% of the starting alkene ketone converted to the cyclopropanated ketone.

The NMR spectrum of the Bicyclo[13.1.0]hexadecan-4-one is as follows: 0.6 ppm (m, 1H); 0.7 ppm (s, 2H); 0.9 ppm (m, 1H); 1.1 ppm (s, 1H); 1.2-1.4 ppm (m, 12H); 1.5 ppm (m, 5H); 1.7 ppm (m, 2H); 1.8 ppm (m, 1H); 2.1 ppm (s, 1H); 2.3-2.5 ppm (m, 3H); 3.6 ppm (m, 1H).

EXAMPLE B

Preparation of 9-Oxa-bicyclo[15.1.0]octadecan-8-one

To a dry 500 ml multi-neck round bottom flask fitted with an air stirrer, nitrogen inlet condenser and an addition funnel 8 g of ZnCu, 26 g of $CH_2I_2$, 100 ml of $Et_2O$ and 2 crystals of $I_2$, were added and stirred. 12 g of oxacycloheptadec-8-en-2-one were added to the mixture and the mixture was heated to reflux. In 4 hours, first sample was taken at 35° C. The mixture was left to age overnight. Next morning, the mixture was quenched with saturated $NH_4Cl$, aqueous layer separated and the organic layer washed with $NaHCO_3$. The organic layer was then dried over anhydrous $MgSO_4$.

The gas chromatography test indicated that 8.1% of the starting alkene lactone converted to the cyclopropanated lactone.

The NMR of 9-Oxa-bicyclo[15.1.0]octadecan-8-one is as follows: 0.0-0.2 ppm (m, 1H); 0.3 ppm (s, 1H); 0.4 ppm (s, 1H); 0.5 ppm (s, 1H); 0.8 ppm (m, 1H); 1.3 ppm (s, 14H); 1.6 ppm (m, 6H); 1.8 ppm (d, 1H); 2.0 ppm (m, 2H); 2.3 ppm (s, 2H); 4.1 ppm (m, 2H); 5.1 ppm (m, 1H).

EXAMPLE C

Preparation of Bicyclo[14.1.0]heptadecan-5-one

To a dry 500 ml multi-neck round bottom flask fitted with an air stirrer, nitrogen inlet condenser and an addition funnel 2.9 g of 5-cyclohexadecen-1-one and 25 ml of Methyl Tertiary Butyl Ether (MTBE) were added. 21.8 ml of 1.1 M solution of $Et_2Zn$ in toluene was added via syringe while stirring. 23 g (6.9 ml) of $CH_2I_2$ was added all at once. The mixture was heated to 60° C. and the first sample was taken. The gas chromatography test indicated that 76.3% of the starting alkene ketone converted to the cyclopropanated ketone. 5 ml of $Et_2Zn$ were added to the mixture and the mixture was stirred for 2 hours. A second sample was taken. The gas chromatography test indicated that 81.6% of the starting alkene ketone converted to the cyclopropanated ketone. Another 5 ml of $Et_2Zn$ were added to the mixture and the mixture was stirred for 2 hours. A second third was taken. The gas chromatography test indicated that 83.6% of the starting alkene ketone converted to the cyclopropanated ketone. The mixture was left to age overnight. Next morning, the mixture was quenched with saturated $NH_4Cl$, aqueous layer separated and the organic layer washed with 200 ml of brine. The organic layer was then dried over anhydrous $MgSO_4$.

The NMR of the Bicyclo[14.1.0]heptadecan-5-one is as follows: 0.2 ppm (d, 2H); 0.4 ppm (s, 2H); 0.6 ppm (m, 1H); 0.7 ppm (s, 2H); 0.8 ppm (m, 1H); 1.1 ppm (m, 3H); 1.2-1.5 ppm (s, 39H); 1.6-1.8 ppm (m, 11H); 2.1 ppm (s, 3H); 2.2-2.7 ppm (m, 10H); 5.2-5.5 ppm (m, 2H).

EXAMPLE D

Preparation of Bicyclo[15.1.0]octadecan-9-one

To a dry 500 ml multi-neck round bottom flask fitted with an air stirrer, nitrogen inlet condenser and an addition funnel 3 g of 9-cycloheptadecene-1-one and 70 ml of Methyl Tertiary Butyl Ether (MTBE) were added. 21.8 ml of 1.1 M solution of $Et_2Zn$ in toluene was added via syringe while stirring. 23 g (6.9 ml) of $CH_2I_2$ was added all at once. The mixture was heated to 60° C. and the first sample was taken. The gas chromatography test indicated that 77.3% of the starting alkene ketone converted to the cyclopropanated ketone. The mixture was left to age overnight. Next morning, the mixture was quenched with saturated $NH_4Cl$, aqueous layer separated and the organic layer washed with 200 ml of brine. The organic layer was then dried over anhydrous $MgSO_4$.

The NMR of the Bicyclo[15.1.0]octadecan-9-one is as follows: 0.5 ppm (s, 1H); 0.6 ppm (s, 2H); 1.1 ppm (d, 2H); 1.3 ppm (s, 11H); 1.4 ppm (s, 8H); 1.6 ppm (s, 4H); 2.4 ppm (m, 4H).

EXAMPLE E

Preparation of 5-Oxa-bicyclo[14.1.0]heptadecan-6-one

To a dry 500 ml multi-neck round bottom flask fitted with an air stirrer, nitrogen inlet condenser and an addition funnel 16 g of ZnCu, 200 ml of Methyl Tertiary Butyl Ether (MTBE) were added and 3 crystals of $I_2$ were added and stirred. 104 g of $CH_2I_2$ was added while stirring. The mixture was heated maintained at 60° C. 48 g of oxacyclohexadec-12-en-2-one was added dropwise over 90 minutes. In another 20 minutes a first sample was taken. The gas chromatography test indicated that 45.9% of the starting alkene lactone converted to the cyclopropanated lactone at this point. In 2 hours a second sample was taken. The gas chromatography test indicated that 62.1% of the starting alkene lactone converted to the cyclopropanated lactone. The mixture was cooled to 30° C., quenched with saturated $NH_4Cl$, aqueous layer separated and the organic layer washed with 200 ml of brine. The organic layer was then dried over anhydrous $MgSO_4$.

The NMR of the 5-Oxa-bicyclo[14.1.0]heptadecan-6-one is as follows: 0.2 ppm (m, 1H); 0.3 ppm (m, 1H); 0.4 ppm (m, 2H); 0.6-0.8 ppm (d, 1H); 1.2-1.5 ppm (d, 13H); 1.7 ppm (s, 3H); 1.8 ppm (m, 2H); 2.1 ppm (s, 1H); 2.3-2.5 ppm (m, 2H); 4.0-4.1 ppm (m, 1H); 4.3 ppm (m, 1H).

EXAMPLE F

Preparation of 3-Methyl-6-oxa-bicyclo[13.1.0]hexadecane-7-one

To a dry 200 ml multi-neck round bottom flask fitted with an air stirrer, nitrogen inlet condenser and an addition funnel 2.9 g of 99% 3-Methyl-cyclopentadec-5-enone and 25 ml of Methyl Tertiary Butyl Ether (MTBE) was added. The resulting mixture was stirred for 5 minutes. 21.8 ml of 1.1 M $Et_2Zn$ were added via syringe. After the temperature of the mixture stabilized, 23 g of $CH_2I_2$ were added while stirring. In about 60 minutes a first sample of the product was taken. The gas chromatography test indicated that 39.3% of the starting alkene lactone converted to the cyclopropanated lactone. The mixture was left to age overnight. Next morning, the mixture was quenched with saturated $NH_4Cl$, aqueous layer separated and the organic layer washed with $NaHCO_3$. The organic layer was then dried over anhydrous $MgSO_4$.

The gas chromatography test indicated that 39.3% of the starting alkene ketone converted to the cyclopropanated ketone.

The NMR spectrum of the 3-Methyl-6-oxa-bicyclo [13.1.0]hexadecane-7-one is as follows: 0.6 ppm (m, 2H); 0.8 ppm (s, 1H); 0.9 ppm (m, 1H); 1.1 ppm (m, 3H); 1.2-1.4 ppm (m, 11H); 1.7 ppm (m, 1H); 2.1 ppm (s, 1H); 2.2-2.4 ppm (m, 2H); 2.5 ppm (m, 1H).

EXAMPLE G

Preparation of Bicyclo[14.1.0]heptadecan-8-one

To a dry 500 ml multi-neck round bottom flask fitted with an air stirrer, nitrogen inlet condenser and an addition funnel 6.7 g of ZnCu, 80 ml of Methyl Tertiary Butyl Ether (MTBE) and one iodine crystal were added. The resulting mixture was stirred until color faded. 30 g of $CH_2I_2$ was added and the mixture was heated to reflux. 22 g of 99% pure cyclohexadec-8-one was added dropwise. After the mixture turned grayish pink color, a first sample was taken. The mixture was cooled, quenched with 100 ml of saturated $NH_4Cl$ and stirred for 15 minutes. The mixture was allowed to settle, the aqueous layer was separated, and the organic layer was extracted with two 50 ml portions of toluene. Toluene was added to the crude sample and dried over anhydrous $MgSO_4$.

The NMR spectrum of the Bicyclo[14.1.0]heptadecan-8-one is as follows: 0.2 ppm (m, H); 0.4 ppm (s, H); 0.6-0.7 ppm (m, H); 1.1 ppm (s, H); 1.2-1.5 ppm (m, 10H); 1.6 ppm (m, H); 1.7 ppm (m, H); 1.8 ppm (m, 2H); 2.0 ppm (s, H); 2.2 ppm (m, H); 2.5 ppm (m, H); 2.6 ppm (m, H).

EXAMPLE H

Incorporation of Bicyclo[13.1.0]hexadecan-4-one into a Fragrance Formulation

| Name | Parts |
| --- | --- |
| ALLYL CAPROATE | 0.50 |
| BENZYL ACETATE | 130.00 |
| CITRAL | 0.50 |

-continued

| Name | Parts |
| --- | --- |
| CITRONELLOL | 50.00 |
| CITRONELLYL ACETATE | 110.00 |
| COUMARIN | 11.00 |
| BICYCLO[13.1.0]HEXADECAN-4-ONE | 16.00 |
| DAMASCENONE | 1.00 |
| ETHYL CAPROATE | 1.00 |
| ETHYL-2-METHYL BUTYRATE | 1.00 |
| GERANIOL | 65.00 |
| HEXENYL ACETATE, CIS-3 | 15.00 |
| HEXYL ACETATE | 2.25 |
| IONONE ALPHA | 12.00 |
| IONONE BETA | 12.00 |
| ISO AMYL ACETATE | 0.25 |
| LINALOOL | 45.00 |
| LINALYL ACETATE | 130.00 |
| LYRAL | 30.00 |
| MANDARIN OIL MD REF A LMR | 12.50 |
| METHYL ANTHRANILATE | 30.00 |
| MUSKALACTONE | 25.00 |
| NONADIENAL, TRANS-2-CIS-6 | 15.00 |
| ORANGE OIL BITTER WI | 12.50 |
| ORANGE OIL SWEET | 25.00 |
| PETITGRAIN | 45.00 |
| PHENYL ACETALDEHYDE | 2.00 |
| PHENYL ETHYL ALCOHOL | 100.00 |
| TAGETTE OIL EGYPT MD REF A LMR | 7.50 |
| TERPINEOL | 80.00 |
| UNDECALACTONE GAMMA | 1.00 |
| VETIVERT OIL HAITI MD REF A LMR | 12.00 |
| Total | 1000.00 |

The fragrance was described as having sweet, powdery and floral tones.

EXAMPLE I

Incorporation of Bicyclo[14.1.0]heptadecan-8-one into a Fragrance Formulation

Demonstration Formula (Shower Gel) with Bicyclo[14.1.0]Heptadecan-8-One

| Name | Parts |
| --- | --- |
| 3-Dodecenal, 10% In Dipropylene Glycol | 25.00 |
| Amyl Salicylate | 50.00 |
| Benz Acetate | 65.00 |
| Benzyl Cinnamate | 35.00 |
| Benzyl Salicylate | 150.00 |
| Citronellol Coeur | 50.00 |
| Cresyl Phen Acetate Para | 1.00 |
| Ethylene Brassylate | 12.00 |
| Galbaniff | 2.00 |
| Geraniol | 10.00 |
| Bicyclo[14.1.0]Heptadecan-8-One | 40.00 |
| Guaiacwood Oil | 4.00 |
| Hexenyl Salicylate,Cis-3 | 35.00 |
| Hexyl Cinnamic Aldehyde | 200.00 |
| Jasmone Cis | 3.00 |
| Koavol DH | 85.00 |
| Lyral | 135.00 |
| Methyl Anthranilate | 8.00 |
| Muskalactone | 10.00 |
| Phenyl Ethyl Phenyl Acetate | 35.00 |
| Styralyl Acetate | 15.00 |
| Veramoss | 15.00 |
| Ylang Oil | 15.00 |
| Total weight | 1000.00 |

The fragrance was described as having sweet, powdery and floral tones.

EXAMPLE K

Incorporation of
9-Oxa-bicyclo[15.1.0]octadecan-8-one into a
Fragrance Formulation

| Name | Parts |
| --- | --- |
| ALLYL AMYL GLYCOLATE | 1.00 |
| BENZYL ACETATE | 10.00 |
| BENZYL SALICYLATE | 55.00 |
| BERGAMOT OIL | 35.00 |
| CASHMERAN | 4.00 |
| CEDRENYL ACETATE | 20.00 |
| CITRONELLOL | 50.00 |
| COUMARIN | 25.00 |
| CYCLOGALBANIFF | 3.00 |
| 9-OXA-BICYCLO[15.1.0]OCTADECAN-8-ONE | 7.50 |
| DAMASCONE, DELTA | 0.40 |
| ETHYL VANILLIN | 1.00 |
| EUGENOL | 40.00 |
| GALAXOLIDE | 90.00 |
| GALBANUM OIL REF A LMR | 0.10 |
| GERANIOL | 13.00 |
| HEDIONE | 80.00 |
| HELIONAL | 6.00 |
| HELIOTROPINE | 20.00 |
| HEXENYL SALICYLATE, CIS-3 | 13.00 |
| IONONE BETA | 10.00 |
| ISO E SUPER | 60.00 |
| JASMIN ABS EGYPT LMR | 5.00 |
| LILIAL | 40.00 |
| LINALOOL | 80.00 |
| LINALYL ACETATE | 65.00 |
| LYRAL | 40.00 |
| METHYL ANTHRANILATE | 8.00 |
| METHYL IONONE GAMMA | 55.00 |
| MUSKALACTONE | 25.00 |
| OLIBANUM COEUR DEP 50 PCT | 6.00 |
| PATCHOULI OIL | 35.00 |
| SANDALORE | 20.00 |
| SANJINOL | 20.00 |
| STYRALYL ACETATE | 10.00 |
| VANILLIN | 13.00 |
| VERAMOSS | 4.00 |
| VERTOFIX | 25.00 |
| YLANG OIL | 5.00 |
| Total | 1000.00 |

The fragrance was described as having sweet, powdery and floral tones.

What is claimed is:

1. A compound of formula

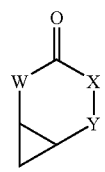

wherein X is selected from the group consisting of CH and $CH_2$;

Y is a saturated or unsaturated straight or branched hydrocarbon chain consisting of 1 to 20 carbon atoms; and W is a saturated or unsaturated straight or branched hydrocarbon chain consisting of 1 to 20 carbon atoms, with the proviso that the combined number of the carbon atoms in Y and W is at least 5.

2. The compound of claim 1, wherein the compound is

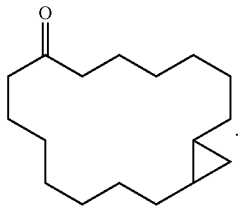

3. A fragrance formulation containing an olfactory effective amount of the compound of claim 2.

4. A fragrance product containing a compound of claim 2.

5. A fragrance formulation containing an olfactory effective amount of a mixture containing bicyclo[14.1.0]heptadecan-8-one and cyclohexadec-3-enone.

6. A fragrance formulation of claim 5, wherein the ratio of bicyclo[14.1.0]heptadecan-8-one to cyclohexadec-3-enone in the mixture is from about 1.5:1 to about 4:1.

* * * * *